(12) United States Patent
Sharma

(10) Patent No.: US 11,596,335 B2
(45) Date of Patent: Mar. 7, 2023

(54) SYSTEM AND METHODS FOR REMOTELY MONITORING LEAN MUSCLE MASS

(71) Applicant: NxGen Med LLC, Stoneham, MA (US)

(72) Inventor: Rakshit Sharma, Bedford, MA (US)

(73) Assignee: NXGEN MED LLC, Stoneham, MA (US)

( * ) Notice: Subject to any disclaimer, the term of this patent is extended or adjusted under 35 U.S.C. 154(b) by 95 days.

(21) Appl. No.: 16/663,150

(22) Filed: Oct. 24, 2019

(65) Prior Publication Data

US 2020/0129107 A1 Apr. 30, 2020

Related U.S. Application Data

(60) Provisional application No. 62/756,866, filed on Nov. 7, 2018, provisional application No. 62/750,064, filed on Oct. 24, 2018.

(51) Int. Cl.
*A61B 5/22* (2006.01)
*A61B 5/00* (2006.01)
*G16H 20/30* (2018.01)
*G16H 40/67* (2018.01)

(52) U.S. Cl.
CPC ............ *A61B 5/225* (2013.01); *A61B 5/0004* (2013.01); *A61B 5/0022* (2013.01); *A61B 5/486* (2013.01); *A61B 5/7275* (2013.01); *A61B 5/742* (2013.01); *G16H 20/30* (2018.01); *G16H 40/67* (2018.01)

(58) Field of Classification Search
CPC ..... A61B 5/225; A61B 5/0004; A61B 5/0022; A61B 5/7275; A61B 5/742; A61B 5/486; A61B 5/224; A61B 5/4842; A61B 5/0537; A61B 2562/04; G16H 20/30; G16H 40/67
See application file for complete search history.

(56) References Cited

U.S. PATENT DOCUMENTS

2006/0161073 A1 7/2006 Singer et al.
2012/0094260 A1 4/2012 Akins et al.
2015/0245789 A1 9/2015 Dromerick et al.
(Continued)

OTHER PUBLICATIONS

Massy-Westropp, Nicola M et al. "Hand Grip Strength: age and gender stratified normative data in a population-based study." BMC research notes vol. 4 127. Apr. 14, 2011, doi:10.1186/1756-0500-4-127 (Year: 2011).*

(Continued)

*Primary Examiner* — Matthew Kremer
*Assistant Examiner* — Kyle W. Kretzer
(74) *Attorney, Agent, or Firm* — Young Basile Hanlon & MacFarlane, P.C.

(57) ABSTRACT

Systems and methods for lean muscle mass monitoring of patients and for identifying and treating at least one of Cachexia or Sarcopenia are disclosed. The system may include a dynamometer provided to patients, the dynamometer being configured to perform remote monitoring. The dynamometer may be used and data may be collected by patients without the supervision of a healthcare professional. Using the collected data, lean muscle mass may be tracked over time, to provide fast and accurate assessment of conditions. Using such an assessment, early treatment options can be targeted to patients to avoid progression into various disease states, for examples, more severe states of at least one of Cachexia or Sarcopenia.

14 Claims, 4 Drawing Sheets

(56) References Cited

U.S. PATENT DOCUMENTS

2016/0220863 A1* 8/2016 Braier .................... A63B 23/16
2017/0076052 A1* 3/2017 Phillips ................. G16H 70/20
2018/0064386 A1* 3/2018 Johns ................ A61B 5/14546
2018/0168530 A1* 6/2018 Wear ...................... A61B 5/225

OTHER PUBLICATIONS

International Search Report and Written Opinion dated Jan. 6, 2020 in connection with International Application No. PCT/US2019/057839.

* cited by examiner

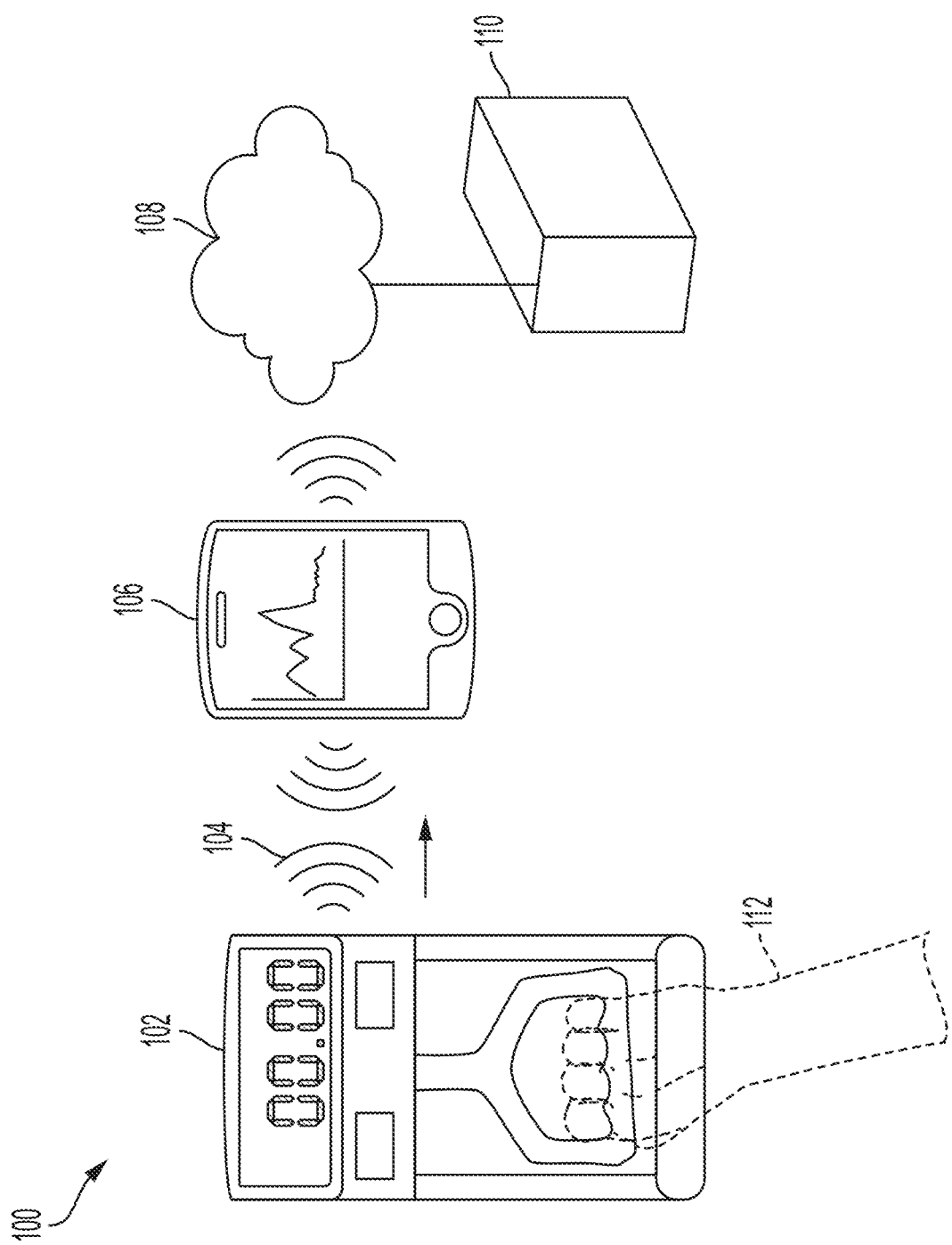

SYSTEM AND METHODS FOR REMOTELY MONITORING LEAN MUSCLE MASS

RELATED APPLICATIONS

This application claims priority under 35 U.S.C. § 119(e) to U.S. Provisional Application Ser. No. 62/750,064, titled "SYSTEM AND METHODS FOR REMOTELY MONITORING LEAN MUSCLE MASS", filed on Oct. 24, 2018, which is herein incorporated by reference in its entirety.

This application claims priority under 35 U.S.C. § 119(e) to U.S. Provisional Application Ser. No. 62/756,866, titled "SYSTEM AND METHODS FOR IMPROVING TREATMENT TOLERABILITY FOR PATIENTS", filed on Nov. 7, 2018, which is herein incorporated by reference in its entirety.

BACKGROUND

One of the biggest unmet needs in medicine/clinical world is a treatment for Cachexia or loss of skeletal muscle and adipose tissue mass. Cachexia progresses in three stages namely pre-cachexia, cachexia and refractory cachexia and if diagnosed/caught early in pre-cachexia or even cachexia stage can be avoided or managed with a combination of targeted nutrition, exercise, physical therapy, etc. Some conventional techniques for identifying cachexia occur through expensive investigations like CT-scans or DEXA scans—for which patients have to go to hospital or radiology center to get that scan, which are expensive and inconvenient and cannot be repeated frequently

BRIEF SUMMARY OF DISCLOSURE

It is realized that improved systems and methods for identifying and treating at least one of Cachexia or Sarcopenia are needed. Stated broadly various aspects describe systems and methods for improving lean muscle mass monitoring or patients. In various embodiments, remote monitoring devices can be provided to patients, the data analyzed, and early treatment options can be targeted to patients to avoid progression into various disease states.

According to one aspect, a system for improving tracking and analysis of lean muscle mass or lean body mass is provided. The system tracks lean muscle mass over time to provide faster and more accurate assessment of conditions, for example, at least one of Cachexia or Sarcopenia. The inventor has recognized and appreciated that strength may a better parameter than other existing, conventional parameters in predicting at least one of Cachexia or Sarcopenia.

According to some aspects of the present disclosure, there is provided a system for improving analysis of lean muscle mass or lean body mass. The system comprises a dynamometer configured to determine hand grip strength measurements. The dynamometer includes a communication component configured to pair with a mobile device or health service platform. The dynamometer is configured to capture hand grip strength measurements for a patient according to a system defined frequency and communicate the hand grip strength measurements to the mobile device or the health service platform. The system comprises a health service platform, including at least a first cloud based resource, configured to receive the hand grip strength measurements; fit the hand grip strength measurements to a respective model of a state of the patient; responsive to fitting the hand grip strength measurements to the respective model, generate an indication of an improving, a worsening, or a same state; and based on the improving, the worsening, or the same state of the patient, update the system defined frequency.

According to some embodiments, the system is further configured to, based on a worsening state of the patient, determine an first interventional action to be presented to the patient.

According to some embodiments, the system is further configured to present the first interventional action to the patient According to some embodiments, the system is further configured to, after presenting the first interventional action to the patient, based on persistence of the worsening state of the patient, determine an escalated second interventional action.

According to some embodiments, the system is configured to determine the first interventional action without user input.

According to some embodiments, the health service platform automatically changes the system defined frequency responsive to determining a new state of the patient.

According to some embodiments, the health service platform fits the hand grip strength measurements taken over time to the respective model of patient state and a potential treatment option.

According to some embodiments, the system displays the potential treatment option to a healthcare professional.

According to some aspects of the present disclosure, there is provided a method of analyzing lean muscle mass or lean body mass, the method comprising capturing hand grip strength measurements for a patient according to a system defined frequency using a dynamometer including a communication component configured to pair with a mobile device or health service platform; communicating the hand grip strength measurements to a mobile device or a health service platform using the dynamometer; fitting the hand grip strength measurements to a respective model of a state of the patient using a health service platform including at least a first cloud based resource; responsive to fitting the hand grip strength measurements to the respective model, generating an indication of an improving, a worsening, or a same state of the patient using the health service platform; based on the improving, the worsening, or the same state of the patient, updating the system defined frequency using the health service platform.

According to some embodiments, the method further comprises, based on a worsening state of the patient, determining an first interventional action to be presented to the patient.

According to some embodiments, the method further comprises presenting the first interventional action to the patient According to some embodiments, the method further comprises, after presenting the first interventional action to the patient, based on persistence of the worsening state of the patient, determining an escalated second interventional action.

According to some embodiments, the method further comprises determining the first interventional action without user input.

According to some embodiments, the method further comprises automatically changing the system defined frequency responsive to determining a new state of the patient.

According to some aspects of the present disclosure, there is provide at least one non-transitory computer-readable storage medium having encoded thereon executable instructions that, when executed by at least one processor, cause the at least one processor to carry out a method of analyzing lean muscle mass or lean body mass. The method comprises capturing hand grip strength measurements for a patient according to a system defined frequency; communicating the hand grip strength measurements to a mobile device or a health service platform; fitting the hand grip strength measurements to a respective model of a state of the patient; responsive to fitting the hand grip strength measurements to the respective model, generating an indication of an improving, a worsening, or a same state of the patient; and based on the improving, the worsening, or the same state of the patient, updating the system defined frequency.

According to some embodiments, the method further comprises, based on a worsening state of the patient, determining an first interventional action to be presented to the patient.

According to some embodiments, the method further comprises presenting the first interventional action to the patient According to some embodiments, the method further comprises, after presenting the first interventional action to the patient, based on persistence of the worsening state of the patient, determining an escalated second interventional action.

According to some embodiments, the method further comprises determining the first interventional action without user input.

According to some embodiments, the method further comprises automatically changing the system defined frequency responsive to determining a new state of the patient.

BRIEF DESCRIPTION OF DRAWINGS

FIG. 1 is a block diagram of various system components according to one embodiment;

DETAILED DESCRIPTION

Figure 2B:
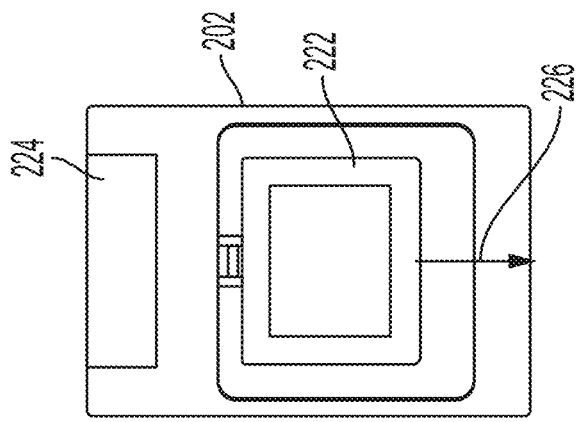
FIGS. 2A and 2B illustrate some functions and data flows executed by the example system components.

Cachexia is a muscle weakness in the presence of a disease such as cancer. In some embodiments, the system may provide an assessment of Sarcopenia. Sarcopenia is a muscle weakness rooted in adverse muscle changes that accrue across a lifetime; Sarcopenia is common among adults of older age but can also occur earlier in life. Both Cachexia and Sarcopenia may be preceded by malnutrition. An assessment of at least one of Sarcopenia and Cachexia may be provided according to various techniques described below.

A primary parameter of Sarcopenia may be low muscle strength. Muscle strength may be a most reliable measure of muscle function. According to some standards, Sarcopenia is probable when low muscle strength is detected. According to some standards, Sarcopenia diagnosis is confirmed by the presence of low muscle quantity or quality. According to some standards, when low muscle strength, low muscle quantity/quality and low physical performance are all detected, Sarcopenia is considered severe.

When measuring muscle strength in determining a diagnosis of at least one of Cachexia or Sarcopenia, grip strength may be used. Grip strength correlates moderately with strength in other body compartments. Accordingly, grip strength may serves as a reliable surrogate for more complicated measures of arm and leg strength. Therefore, grip strength may be a primary diagnostic criterion of at least one of Cachexia or Sarcopenia.

With respect to a Sarcopenia diagnosis, some standards use a grip strength cut-off point of less than 27 kg for men and less than 16 kg for women.

According to one embodiment, a dynamometer incorporates wireless communication circuitry and enables remote measurement, monitoring, and display of grip strength, which the system correlates to lean muscle mass. The dynamometer is paired with a specific patient and configured to communicate with a health platform. The dynamometer is configured to transmit changes in lean body mass or lean muscle mass through intermittent measurement of the hand grip strength. The system is also configured to dynamically adjust remote measurement frequency to improve the accuracy of modelled information, and to improve the speed and efficiency in identifying negative or positive changes in the patient.

According to one aspect, the system is configured to build a time based model of lean muscle mass based on remote measurement of grip strength. Various embodiments of the system integrate with remote hand strength monitors that are distributed and paired with specific patients. The hand strength monitors are configured with Internet connectivity, for example, through wireless cellular networks and/or Bluetooth, wifi, or Zigbee (or other short-range wireless communication standard) enabled components. In one example, the system builds a time based model for each patient linking hand strength measurements taken on system defined intervals to lean muscle mass. The approach matches the current measurements taken over time for each patient and fits those measurement to the closest model. System used the comparison model to provide an indication regarding state of the patient, and for example, to identify patients having Cachexia or trending towards a Cachexia diagnosis.

In some embodiments, the system can tailor remote measurement frequency to the specific patients and system determined trends in the patient measurements and/or model. For example, in patients showing a decrease in lean muscle mass (e.g., based on reductions in hand grip strength over time) the system can change the parameters (e.g., frequency) of measurement. In one example, the system can automatically increase the frequency of measurement to obtain increases in accuracy of the model, and to identify indications of reduced lean muscle mass faster than any conventional approach.

In further embodiments, the system is configured to analyze patient models and identify when further intervention is indicated, faster and more accurately than conventional approaches. In some embodiments, the system is configured to generate the time based model, and analyze the model to evaluate current treatments for effectiveness and improve determinations of declining state or confirm improvement condition.

FIG. 1 shows a dynamometer configured for remote monitoring and pairing with a health service platform. According to one embodiment, a dynamometer includes network communication circuitry for communicating with, for example, a mobile device. In one example, the mobile device can be registered with a patient, and the dynamometer can be configured to pair/communicate only with the patient's mobile device. The mobile device can then transmit collect data to a health platform through an internet connection. In some embodiments, the mobile device acts as an intermediate between the dynamometer and a health service platform. In other examples, the dynamometer can communicate directly with the health platform.

In embodiments where the mobile device acts as an intermediate between a dynamometer and a health services platform, the mobile device and the dynamometer may be paired via Bluetooth, wifi, Zigbee or another short-range communication networks. In some embodiments, the dynamometer may be paired with a mobile device or personal computer by a home network or a hub device (for example, a Bluetooth or Zigbee hub). In such embodiments where the dynamometer is paired with another device, the mobile device or personal computer may act as a display for the patient, prompting the user to obtain measurements using the dynamometer, and providing interventional actions to the patient, discussed in further detail below.

The dynamometer can be configured to prompt the user to take a measurement of their hand strength at regular intervals (e.g., daily, every other day, weekly, etc.) based on system defined frequency. In some alternative embodiments, alerts may be provided to a user through a paired mobile device.

According to some embodiments, the system can be configured to lock a mobile device from use until a grip strength session has been completed. For example, this feature can be implemented as part of a mobile device application that is paired with a dynamometer. In some conventional settings, failure to complete remote monitoring regimes makes such approaches ineffective. In various embodiments, implementing a technological lock out mechanism can be used to ensure participation by end users. In other embodiments, automatic remote support can be triggered in the event that the system detects a missed grip strength exercise. For example the system can be configured to provide video support on how to conduct the session. The video support may be an automated service configured to mimic health professionals to provide support and encouragement to a user while providing instruction.

In other embodiments, the system can identify other users to pair with the current user, and trigger communication sessions between paired users at scheduled grip strength sessions. In various example, the communication sessions can be trigger for grip sessions and/or as remediation/encouragement. In further examples, the system can automatically send pairing request to users and if the response is positive, pair participants to improve regimen compliance.

In further embodiments, the system can be configured to trigger various remediations in response to a detected missed session. In still others, the system can be programmed to escalate intervention approaches. For example, a first missed grip session can trigger the system to monitor upcoming sessions. The monitoring can include determining a proximity of the grip strength device. In one example, the system can create a monitor event to occur at a time period with respect to subsequent data collection points (e.g., 1 hour, 30 minutes, 15 minutes, etc. before a next session). Once the time period is met, the system triggers a proximity test, where a user device determines proximity to a grip strength device. If proximity is determined (e.g., within 15 ft, 30 ft. 50 ft. etc. or within Bluetooth range, within wifi range, etc.) operations can proceed as normal. If proximity is not detected, an automated phone call can be triggered to alert the user of the upcoming test and that the grip strength device is not nearby. Other communication modalities (e.g., e-mail, push notification, text, tweet, social media post/ communication, video call, etc.) can be triggered in the alternative or in conjunction with the automated phone call.

In some examples, the system can locate the measurement device an provide instructions on location. For example, the system can detect the location of a user mobile device and the grip strength device and provide directions on respective location.

In one embodiment, a user interface display can include a find my measurement device display, which can be selected by the user and/or triggered automatically when a user session is scheduled (and for example, the device is proximate to a user location). The location display can be quite simple, showing an arrow and a number of feet to the measurement device. In various embodiments, a user can select a found option in a user interface once located. In another embodiment, the system can automatically transition from the location interface once the distance to the measurement device is sufficient small (e.g., <1 ft). In other examples, the system can require sufficiently small distance and a period of time before transitioning out of the location interface automatically. In response to automatic transition, the user interface can display a return to locator screen icon for selection by the user. The location of the measurement device may be determined by the mobile device using a communication protocol such as Bluetooth or ultra-wideband.

Alternatively or additionally to the find my measurement device display, the mobile device may include a display including a user interface element which, when selected by the user, transmits a communication to the measurement device (e.g., a dynamometer), the communication causing the measurement device to emit an audible alert. The audible alert may allow the user to locate the measurement device more efficiently.

Figure 4B:
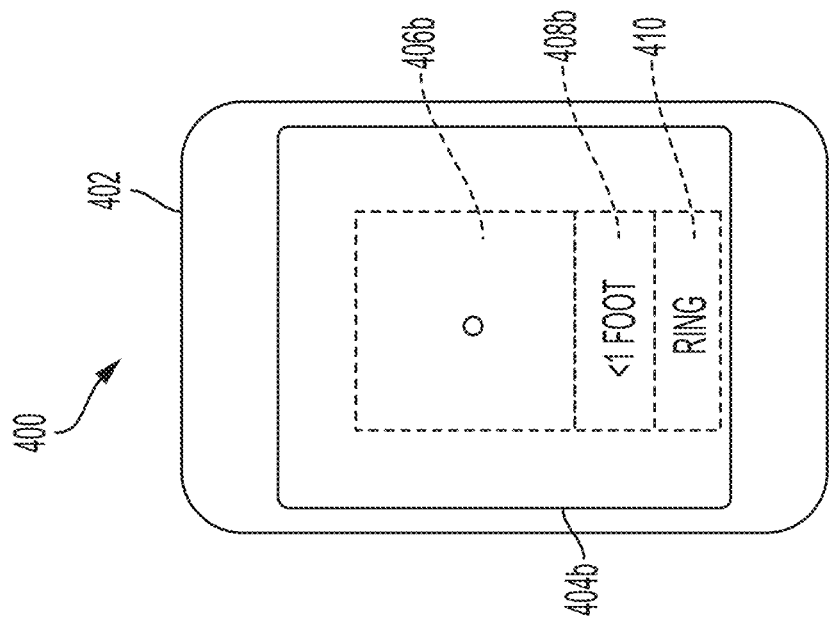
FIGS. 4A and 4B illustrate some exemplary user interface displays executed on a mobile device in connection with measurement device location and audible alert functions.
Figure 4A:
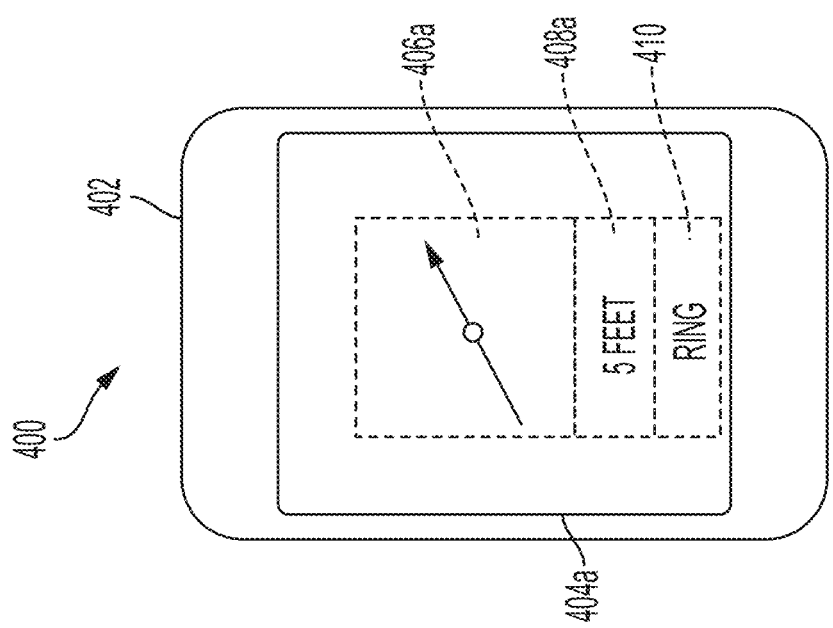

For example, FIGS. 4A and 4B show some exemplary user interface displays executed on a mobile device in connection with measurement device location and audible alert functions. System 400 may include a mobile device 402, as well as a measurement device and/or a communication network. As shown in FIG. 4A, mobile device 402 may have a first user interface display 404a. According to some embodiments, the first user interface includes a first direction display 406a, a first distance display 408a and an audible alert user interface element 410. In FIG. 4A, the first direction display 406a is an arrow pointing in the direction of the measurement device. The first distance display 408a states the approximate distance to the measurement device, along the direction, here 5 feet. The user may select the audible alert user interface element 410 to ring the measurement device.

As shown in FIG. 4B, mobile device 402 may have a second user interface display 404b. The second user interface display may be displayed by a mobile device within a minimum distance of the measurement device, here, 1 foot. According to some embodiments, the second user interface includes a second direction display 406b, a second distance display 408b and an audible alert user interface element 410. In FIG. 4B, the second direction display 406b does not display a distance as the mobile device is within a minimum distance of the measurement device. The second distance display 408b states the minimum distance has been reached, indicating to the user to search the area. The user may select the audible alert user interface element 410 to ring the measurement device. In some embodiments, the audible alert user interface element 410 may be emphasized in the second user interface display 410b to further indicate that the mobile device is within a minimum distance of the measurement device and that the user should therefore ring the measurement device.

In further embodiments, the system can be configured to automatically create a communication session to a live health care provider as another remediation approach to missed sessions, that can be triggered directly or as an escalation from other remediation approaches, and/or in conjunction with other remediation approaches.

In further embodiments, a rescheduler interface can be triggered by the user in response to an upcoming or current data collection session (e.g., hand grip strength test). In various embodiments, the user can push the session to a later time or another day. In some embodiments, the system only permits delay of a certain time (e.g., <1 week) by the user, and requires health provide approval for longer delays (or cumulative delays in excess of the certain time).

According to one embodiment, the rescheduler interface can be triggered automatically in response to the system detecting an impending sessions, and that the measurement device is not within a distance (e.g., system specified and/or a distance unable to be travelled in time available, among other options) of the user.

When in use the dynamometer records the amount of static force in kilograms or pounds that participant hand can squeeze around a dynamometer, and transmits the date wirelessly through blue-tooth and/or cellular data. In some embodiments, the dynamometer includes Bluetooth, wifi, or Zigbee chips and communicates data to mobile device, in other embodiments the dynamometer includes cellular communication circuitry, and communicate with a health service platform (e.g., via GSM/cellular connectivity). In various examples, the dynamometer can be self-configuring. For example, once powered on, the dynamometer can dial home and set up a secure communication channel to a health service platform, or in one alternative, communicate to a patient mobile device and set up a secure communication channel to the mobile device.

In other embodiments, patients can view their measurements based on computer visualization of hand strength over time. Likewise caregivers can access the health platform to review visualizations of hand strength. In some embodiments, the system can also provide visualizations of diagnostic models that best fit the patients data along with a system determined indication for patient health state (e.g., pre-Cachexia, improving, or unchanged, among other examples). In various embodiments, the dynamometer is connected to a health platform that models the user data to identify trends and/or provide indications of health state. In one example, the system uses indication of health state to identify treatment options (e.g., change of nutrition, etc.) that should be executed. The system can evaluate current treatment and/or update treatment options to determined effectiveness long before conventional approaches can make the same determination.

In some settings, the system is configured to dynamically alter frequency of measurement requests and/or prompts made to the user, responsive to changes in health state (e.g., worsening, improving, etc.). In one example, the system dynamically increased monitoring frequency when worsening states are identified or indicated. In this manner, the system improves diagnostic accuracy faster and more efficiently than known approaches. In another example, improving conditions can lead to reduced frequency of measurement, effectively reducing the computational burden on the system (e.g., reducing processing, reducing network bandwidth, memory usage, and storage, among other options).

Various embodiments of the dynamometer can incorporate additional functions and/or display. For example, the dynamometer can be configured to measure and numerically display hand grip strength for Right and Left hand in pounds or KGs to the user. Further, the dynamometer can transmit the captured dates to data warehouse operating in the cloud (e.g., health platform). The transmission can occur via at least one of cellular transmission, Bluetooth, wifi, or Zigbee, or other connection via a smartphone and associated application installed on the mobile device that is connected to the data warehouse. In one example, the dynamometer has a digital display, on/off switch, intuitive user interface/toggle for a memory register of last 30 readings/measurement records.

In one embodiment, the device is configured to display prompts the user to measure non-dominant hand grip strength first and then for the dominant hand. The dominant hand setting can be input by the user or stored as part of a user profile when the user is registered for the system. In various embodiments, the dynamometer can be independently power by internal replaceable batteries or can be plugged into power outlets.

According to one embodiment, users tracking/monitoring their lean body mass or lean muscle mass over a period of time turn on the dynamometer to take measurements as needed or when prompted (e.g., by the dynamometer or mobile device push message, etc.). In one example, the user beings in a standing/upright position and arms at their sides, elbows slightly bent and squeezes the dynamometer with their non-dominant hand as hard as possible. The user is prompted to wait for 10-20 seconds and squeeze again. The dynamometer is configured to provide audio confirmation and/or prompts during measurement. For example, the device will beep and ask the user to squeeze the dynamometer with their dominant hand as hard as possible, wait for 10-20 seconds and squeeze again. According to another embodiment, once four hand grip measurements are recorded, the device is configured to transmit the data, and provide audio and/or visual confirmation (e.g., beep and display sent) to the user.

In various embodiments, the timing for measurement is set on the system, which then prompts the user to take measurements as needed. In one example, a defaults measurement frequency can be daily for capturing non-dominant/dominant hand measurements to identify and observe changes in the hand grip strength over extended period of time. In some embodiments, the system can be configured to automatically set a measurement frequency for a user—for example, for patients undergoing nutritional therapy, daily measurements can be used. Where the system identifies worsening measurements, the system can increase measurement frequency (e.g., twice a day) or increase every other day to daily, weekly to 3 times a week, etc. Where user condition is improving, the system can automatically reduce measurement frequency and limit use of computational resources for monitoring "good" conditions.

According to some embodiments, a patient considered at risk of at least one of Cachexia, Sarcopenia, or malnutrition will measure grip strength once per day. According to some embodiments, a patient recovering from surgery or illness will measure grip strength once per day. According to some embodiments, a patient over an age of 60 years, who is not considered at risk of at least one of Cachexia, Sarcopenia, or malnutrition, who is not recovering from surgery or illness will measure grip strength once per week. The inventor has recognized that these frequencies may provide a sufficiently accurate monitoring of at risk patients and patients who are not presently considered at risk. Conventionally, in clinical settings, the hand grip of a patient might be recorded once a month when they are undergoing any treatment. This conventional measurement of hand grip strength requires the patient to physically visit the hospital or other healthcare facility during treatment or at an annual physical check-up. In the present system, a dynamometer is with the patient and all recording is wireless or otherwise automatic, facilitating the above-described daily or weekly recording results, resulting in more accurate data.

Additionally, technological triggers and responses can be configured to encourage the end user to perform their measurement routine, and/or impose restrictions until the routine is followed. Advanced warnings and the re-scheduler interface improves measurement compliance over known approaches and significantly improves the ability to detect issues and to implement treatment before other conventional approaches.

The system can build various models of the user based on grip strength measurements. For example, hand grip strength is a reliable measure of muscle strength/lean body mass. Where measured and tracked, for example, daily and over extended periods of time, the model is immensely informative of the function/performance status of the user and whether that user is improving or declining in condition. Further, the captured date can also be informative where users are undergoing any type of interventions (e.g., nutrition treatment) to improve muscle strength or lean body mass and to determine more accurately and efficiently over convention approaches if those interventions are being effective and improving the muscle strength over a period of time.

According to various embodiments, the system can recommendation various treatments responsive to analyzed user data. For example, system can identify user's in need of nutritional treatment based upon analysis of on longitudinal measurement of hand grip strength and if that shows declining trend over period of time. The system can generate a personalized regimen of personalized nutrition, exercise, physical therapy or therapeutics depending upon the underlying health conditions. In some embodiments, the system can analyze user data and match a current user to other users who have undergone treatment for similar health states (e.g., grip strength patterns, adjusted for other biometric data (e.g., weight, height, age, sex, etc.), and identify the treatment regimens that were successful for the other user as possible treatment options. In some settings the system can be configured to model treatment approaches, effectiveness, and generate recommendations on treatment options based on matching modeled parameters.

According to various aspects, the system described herein provides increased measuring efficiency. Using the system, a patient records grip strength without requiring the supervision of a medical professional, from the comfort of their home. Accordingly, the system is able to collect far more data than a conventional system can, due to the time required for a patient to schedule in-house appointments, or drive to a healthcare facility, and due to the limited resources of the healthcare facility. In a conventional setting, a healthcare professional such as a nurse, physiotherapist, or clinical worker administers a grip strength test, and manually records readings, followed by another employees recording the readings to a medical record. Accordingly, the present system increases the efficiency of the use of both the patient's and the healthcare facility's limited time and resources.

Example Considerations

As discussed, one of the biggest unmet needs in medicine/clinical world is a treatment for Cachexia or loss of skeletal muscle and adipose tissue mass. In numerous health conditions like muscle wasting disorders, dystrophies or Cancers, cachexia often hinders treatment response and impact, and there are no effective therapies developed to prevent or hamper its progression. Cachexia progresses in three stages namely pre-cachexia, cachexia and refractory cachexia and if diagnosed/caught early in pre-cachexia or even cachexia stage can be avoided or managed with a combination of targeted nutrition, exercise, physical therapy, etc. Conventional approaches for diagnosing cachexia use expensive investigations like CT-scans and/or DEXA scans for which patients have to go to hospital or radiology center to get that scan at significant expense. Moreover, these tests cannot be repeated frequently. Various aspects address some of the shortcomings of conventional approaches using remote enables dynamometers that take measurements (e.g., daily) of the user hand grip strength, transmit the data to a data warehouse in cloud, analyze longitudinal hand grip strength trends for the user and based upon that remotely captured information, intervene to help the patient with appropriate treatment that could be helpful in their case. For example, data which the system may record to a cloud database may include data associated with a certain patient. In some embodiments, the data associated with a certain patient may include the following: grip strength over time, grip strength change amount over time, percent change in grip strength over time, a predetermined grip strength change amount, a predetermined grip strength change percent, and predetermined grip strength threshold, as well as patient identifying data, and records of interventional actions which have been taken and a timeline of the interventional actions.

In some examples, a grip strength measure can trigger the system to automatically open a communication session with a physician, who can review the measurement and prescribe nutrition as a remediation. Upon received the prescription indication from the physical, the system can automatically order the prescribed nutrition and have it delivered to the user's home or address (e.g., immediately, with one hour, within one day, etc.). For example, the system can automatically select a delivery urgency response to information on the respective user. In some embodiments, the system can trigger emergency services automatically for the user.

Various embodiments significantly improve conventional approaches and allow users to benefit and improve their clinical conditions before they are beyond the point of no return, for example, in the refractory cachexia territory. The system is configured to generate longitudinal and remote trend monitoring and analysis of hand grip strength, which the system can also use to inform if a particular intervention is working for the patient. And if not, the system can more efficiently recommend and/or trigger cessation of that treatment (in favor of other treatment) saving the patient and our healthcare system from wasting resources on ineffective interventions.

In some examples, a network connected dynamometer transmits hand grip strength measurements to a health platform/data warehouse via inbuilt GSM chip or using inbuilt Bluetooth, wifi, or Zigbee function to interact with our associated app on a smartphone and using smartphone data connectivity to transmit the hand grip strength measurement data to our health platform/data warehouse. The dynamometer is configured for remote monitoring of changes in hand grip strength/lean muscle mass over period of time and to trigger an intervention response if necessary (e.g., identified by the system).

According to some embodiments, the system has the ability to calculate change in grip strength readings of a patient over a period of time. In some embodiments, the change in grip strength readings is calculated for each individual hand of a patient. In some embodiments, the period of time is the last seven days. In some embodiments, the period of time is the previous month. Using the calculated change of grip strength readings, the system may determine that a predetermined change has occurred, such as a decline. In various embodiments, the predetermined change may comprises a predetermined change amount or predetermined percent change, or a crossing of a predetermined threshold, among other predetermined settings. In response to determining that a predetermined change has occurred, the system may generate a flag or an alert.

The inventor has recognized and appreciated that some conventional measuring techniques employed by conventional dynamometers may be limited. For example, the inventor has recognized and appreciated that if only absolute grip strength is measured, reaction time to Cachexia or Sarcopenia may be limited. The inventor has therefore recognized and appreciated that a dynamometer system as described herein may automatically store historical grip strength data that can be used to identify and predict Cachexia or Sarcopenia early rather than merely determining Cachexia or Sarcopenia has been reached using absolute grip strength. Using a wireless or other system described herein facilitates convenient collection and storage of data to allow Cachexia and Sarcopenia trends to be identified early.

Collection of grip strength data as described herein provides several advantages. Because hand grip data determined by the system is wirelessly or otherwise automatically recorded by the system, no human recording in a diary or on paper is required. Accordingly, challenges associated with human recording, such as chances of error, are minimized. The automatic recording of data results in a more patient-centric approach. The automatic recording of data additionally facilitates the personalization of a dynamometer of program to a particular user, as each device is dedicated and registered to one particular user. This allows a broad range of personalization.

When the system determines a flag, the system may associate the flag with a profile associated with the patient. A healthcare professional viewing the profile associated with the patient may therefore be alerted that the grip strength of the patient has experienced the predetermined change. The healthcare professional accessing the profile may be a care team or a case manager. The flag may include additional information, for example, an indication of the predetermined change amount, or the percent change, or the threshold that was crossed, as well as a total present grip strength, total present change amount, or total percent change percent, an indication of the period of time, an indication of when the flag was generated, and additional patient history information.

In some embodiments, the triggering of the flag can also trigger remediation functions described above (e.g., automated phone calls to walk the user through operation—in case user error is causing flag, remote communication sessions to healthcare provider to supervise testing remotely, communication sessions to other users to coach the current user, etc.)

Alternatively or additionally, the system may determine an alert. When an alert is determined, the system may automatically send the alert to a healthcare professional; such as a care team or case manager to review. Alternatively or additionally, the system may automatically invoke an interventional action. In some embodiments, the invocation of interventional action may comprise invocation of escalating interventional actions. In some embodiments, the interventional action that is automatically invoked may be selected by the system according to the information associated with the predetermined change. In some embodiments, a healthcare professional may predetermine which action are available for the system or invoke. In some embodiments, the healthcare professional may set parameters by which the system selects the actions to be invoked. In various embodiments, actions that the system may automatically invoke may include the following: sending educational physical rehab videos to the user or other educational material (for example, via sending a URL to a patient's mobile device), scheduling an in-home or office appointment with a healthcare professional, notifying specified persons associated with the patient (for example, family members or an emergency contact), prescribing and/or automatically ordering supplemental or other nutrition to be delivered to the patient, or otherwise invoking healthcare intervention.

In some embodiments, educational physical rehab videos or other educational material are automatically sent to the patient. If, after viewing the educational material, and after at least a predetermined time period has elapsed, the decline stops, the system may prompt the user to continue using the dynamometer as usual. However, after viewing the educational material, and after at least a predetermined time period has elapsed, the decline persists, the system may invoke a further escalation interventional actions. In some embodiments, the further escalating interventional action may comprise an alert to a healthcare professional such as a care team or case manager or the ordering of supplemental or other nutrition to be delivered to the patient. Alternatively or additionally, when a decline persists, the system can invoke the sending of physiotherapy or a medical referral for the patient to be investigated further. In some embodiments, this can include remotely supervised grip strength sessions (e.g., by a health care provide and/or other user of the grip strength device, etc.). In various embodiments, the system may record a timeline of interventional actions.

FIG. 1 illustrates various system components according to one embodiment. FIG. 1 depicts a system for improving analysis of lean muscle mass or lean body mass 100 comprising a measurement device 102 (e.g., a dynamometer), a first communication network 104 (e.g., Bluetooth or wireless, etc.), a computing device 106 (e.g., a mobile device), a second communication network 108 (e.g., the internet), and a health platform 110. In some embodiments, a user 112 may operate the measurement device 102.

Figure 2A:
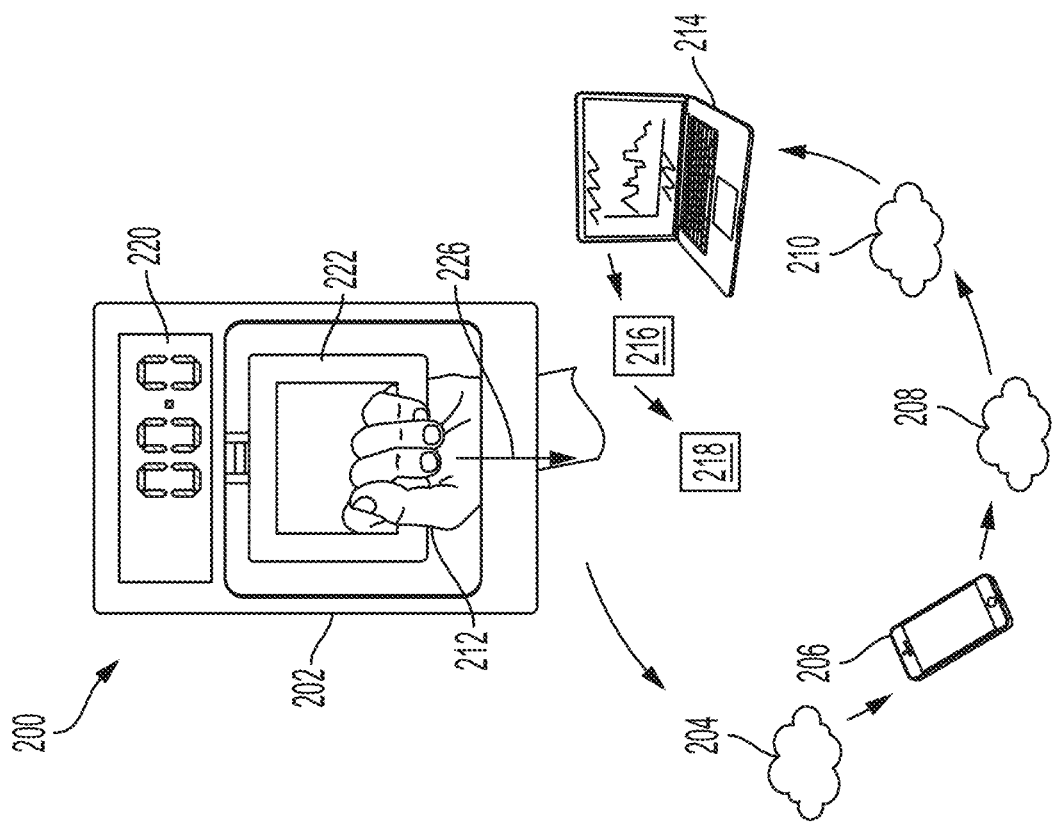

FIGS. 2A and 2B illustrates some functions and data flows executed by example system components. FIG. 2A depicts a system for improving analysis of lean muscle mass or lean body mass 200 comprising a measurement device 202 (e.g., a dynamometer), a first communication network 204 (e.g., Bluetooth or wireless, etc.), a computing device 206 (e.g., a mobile device), a second communication network 208 (e.g., the internet), and a data warehouse 210, and a data visualizer 214 (e.g., a computing device).

In some embodiments a user 212 may operate the measurement device 202 using their hand. FIG. 2A sows a front of a measurement device, and FIG. 2B shows a back of a measurement device. As shown in FIGS. 2A and 2B, measurement device 202 may include a grip 222 to pull down, configured to be pulled by a user along direction 226. As shown in FIG. 2A, measurement device 202 may include a display 220 configured to present information to a user, such as a digital display for measurements. As shown in FIG. 2B, measurement device 202 may include a battery cover 224.

In one exemplary embodiment, measurement device 202 transmits measurements via the first communication network 204 (e.g., Bluetooth) to the computing device 206. Computing device 206 may comprise a smartphone having an app to display readings from a dynamometer. Computing device 206 may transmit data by the second communication network 208 (e.g., cellular data connectivity) to data warehouse 210. Data visualizer 214 may access the data of the data warehouse 210.

From data visualizer 214, with or without user input, alerts 216 and intervention 218 may be triggered. In various embodiments the system triggers alerts to provide intervention based on a decline in strength. Alerts 216 to users may be provided by telephone call, SMS/text, email, banners on smartphones, etc. Intervention 218 may comprise appropriate intervention to regain strength, such as live or remote intervention. Live intervention may comprises a hospital or doctor visit, physical therapy, etc. Remote intervention, e.g., by call (voice or video), may comprise target nutrition, physical therapy, exercise, rehab, etc.

Figure 3:
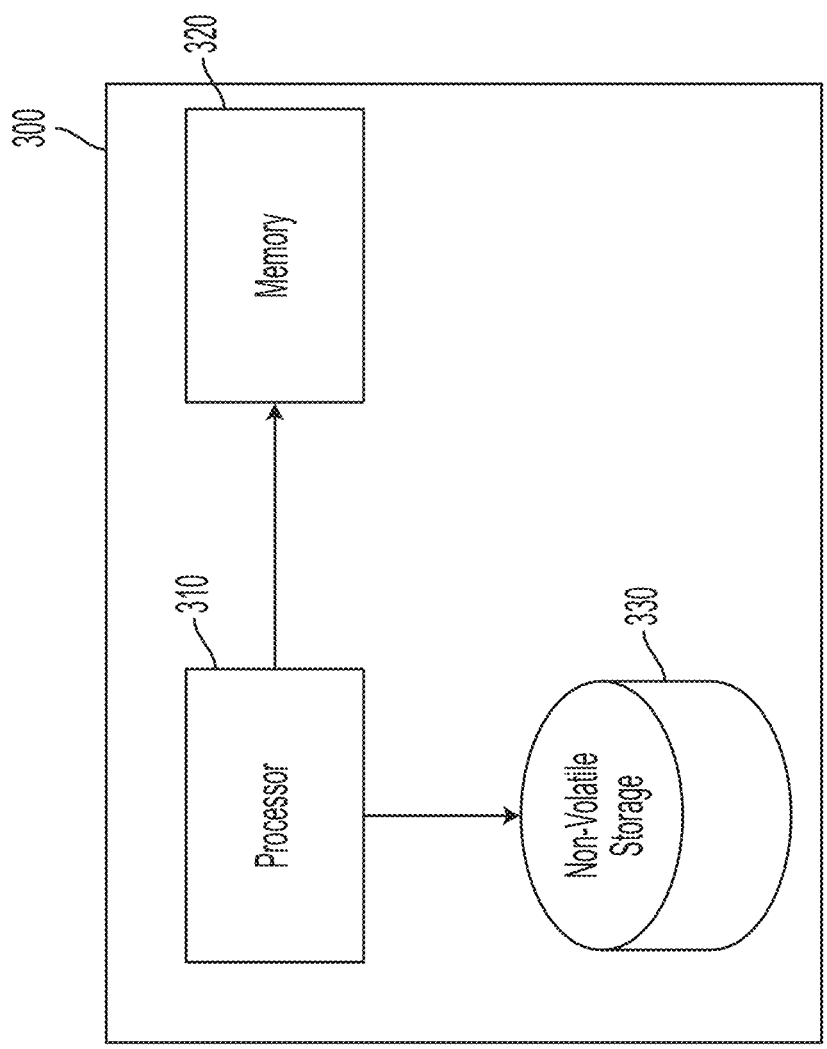
FIG. 3 is a block diagram of a computer system on which various functions can be implemented.

Additionally, an illustrative implementation of a computer system 300 that may be used in connection with any of the embodiments of the disclosure provided herein is shown in FIG. 3. The computer system 300 may include one or more processors 310 and one or more articles of manufacture that comprise non-transitory computer-readable storage media (e.g., memory 320 and one or more non-volatile storage media 330). The processor 310 may control writing data to and reading data from the memory 320 and the non-volatile storage device 330 in any suitable manner. To perform any of the functionality described herein, the processor 310 may execute one or more processor-executable instructions stored in one or more non-transitory computer-readable storage media (e.g., the memory 320), which may serve as non-transitory computer-readable storage media storing processor-executable instructions for execution by the processor 310.

Aspects of the present disclosure maybe applied to systems and methods for improving treatment tolerability for patients, for example, including remote monitoring by medical staff, tracking patient reported symptoms, and/or precision support interventions. Some aspects of the present disclosure may be applied to systems and methods for determining changes in a patient, and making recommendations based on such changes. For example, a variety of data representing conditions such as body weight, temperature, number of steps taken, etc. may be acquired, e.g., using a smartphone or a computer, and based on analysis of those data, one or more recommendations may be made to the patient. In some cases, the patient may also be provided with the recommended treatments, for example, a high calorie meal plan or meal supplements.

For example, certain aspects of the present disclosure may be applied to systems and methods for caring for patients having cancer, or other diseases such as diabetes or heart disease, in which monitoring of a patient's health status, such as their nutritional status, can be important in providing long-term care to the patient.

Patients may be human or a non-human mammal. In some cases, data representing one or more conditions of the subject are determined, e.g., quantitatively. These may be compared against suitable values (e.g., threshold values) to determine a suitable recommendation. In some cases, the recommendation are actually executed, i.e., the patient is treated, or provided treatment, according to the recommendation. For example, the patient may perform the treatment (for example, eating a high calorie meal plan). In some cases, multiple recommendations may be provided to the patient, e.g., based on the various conditions that are determined.

In other examples, identification by the system of a user as high risk can be used to change a user's collection regimen. In one example, a user can have a one per week muscle mass test with a dynamometer. Upon identification of the user as high risk, the system can automatically increase the collection schedule for muscle mass data (e.g., increase testing frequency (e.g., from 1 to 2 times per week, etc.), among other options. In addition, thresholds may be adjusted by the system based on risk stratification—including adjusting thresholds for detecting problematic reduction in muscle mass (e.g., reducing threshold triggers for intervention based on worsening risk score, increasing threshold triggers based on improved risk score/stratification, etc.), increasing collection frequency, decreasing collection frequency, etc.

What is claimed:

1. A system for improving analysis of lean muscle mass or lean body mass, the system comprising:
   a health service platform, including at least a first cloud based resource; and
   a dynamometer configured to determine hand grip strength measurements, the dynamometer including a communication transceiver configured to pair with a mobile device or the health service platform, wherein the dynamometer is configured to:
   remotely capture the hand grip strength measurements for a patient according to a system defined frequency; and
   communicate the hand grip strength measurements to the mobile device or the health service platform;
   wherein at least one of the mobile device and the health service platform, including at least the first cloud based resource is configured to:
   receive the hand grip strength measurements;
   fit the hand grip strength measurements to a respective diagnostic model that best fits a state of the patient;
   responsive to fitting the hand grip strength measurements to the respective diagnostic model:
   provide an indication regarding the state of the patient by:
   using a comparison model to compare with the respective diagnostic model representative of the state of the patient, and based on the comparison:
   identify the state of the patient by categorically classifying the state of the patient into at least one of: Sarcopenia, Cachexia, or pre-Cachexia and generate the indication comprising one of: improving, worsening, or same state within the identified state of the patient;
   based on the identified state and generated indication for the patient, update the system defined frequency at which the dynamometer is to be used by the patient for subsequent measurements of hand grip strength and
   determine a diagnosis for the patient, wherein the determination comprises:
   building a time based model of muscle of the patient using a historical set of the hand grip strength measurements captured remotely by the dynamometer; and
   determining the diagnosis for the patient based on the identified state, the generated indication, and a grip strength change amount over time obtained from the time based model of muscle of the patient; and responsive to the determination of the diagnosis, trigger administration of a treatment of at least one of: pre-Cachexia, Cachexia or Sarcopenia to the patient.

2. The system of claim 1, wherein the system is further configured to, based on the worsening state of the patient, determine a first interventional action to be presented to the patient.

3. The system of claim 2, wherein the system is further configured to present the first interventional action to the patient.

4. The system of claim 3, wherein the system is further configured to, after presenting the first interventional action to the patient, based on persistence of the worsening state of the patient, determine an escalated second interventional action.

5. The system of claim 3, wherein the system is configured to determine the first interventional action without user input.

6. The system of claim 1, wherein the health service platform automatically changes the system defined frequency responsive to determining a new state of the patient.

7. The system of claim 1, wherein the health service platform fits the hand grip strength measurements taken over time to the respective diagnostic model of patient state and a potential treatment option.

8. The system of claim 7, wherein the system displays the potential treatment option to a healthcare professional.

9. A method of analyzing lean muscle mass or lean body mass, the method comprising:

remotely capturing hand grip strength measurements for a patient according to a system defined frequency using a dynamometer including a communication transceiver configured to pair with a mobile device or health service platform;

communicating the hand grip strength measurements by the dynamometer to the mobile device or the health service platform;

fitting the hand grip strength measurements to a respective diagnostic model that best fits a state of the patient using a at least one of the mobile device and the health service platform including at least a first cloud based resource;

responsive to fitting the hand grip strength measurements to the respective diagnostic model:

providing an indication, by at least one of the mobile device and the health service platform, regarding the state of the patient by:

using a comparison model, by at least one of the mobile device and the health service platform, to compare with the respective diagnostic model representative of the state of the patient, and based on the comparison:

identifying, by at least one of the mobile device and the health service platform, the state of the patient by categorically classifying the state of the patient into at least one of: Sarcopenia, Cachexia, or pre-Cachexia and generating, by at least one of the mobile device and the health service platform, the indication comprising at least one of: improving, worsening, or same state within the identified state of the patient;

based on the identified state and generated indication for the patient, updating, by at least one of the mobile device and the health service platform, the system defined frequency at which the dynamometer is to be used by the patient for subsequent measurements of hand grip strength;

determining, by the health service platform, a diagnosis for the patient, comprising:

building a time based model of muscle of the patient using a historical set of the hand grip strength measurements captured remotely by the dynamometer; and determining the diagnosis for the patient based on the identified state, the generated indication, and a grip strength change amount over time obtained from the time based model of muscle of the patient; and responsive to the determination, triggering administration of a treatment of at least one of: pre-Cachexia, Cachexia or Sarcopenia to the patient.

10. The method of claim 9, further comprising, based on the worsening state of the patient, determining a first interventional action to be presented to the patient.

11. The method of claim 10, further comprising presenting the first interventional action to the patient.

12. The method of claim 11, further comprising, after presenting the first interventional action to the patient, based on persistence of the worsening state of the patient, determining an escalated second interventional action.

13. The method of claim 11, further comprising determining the first interventional action without user input.

14. The method of claim 9, further comprising automatically changing the system defined frequency responsive to determining a new state of the patient.

* * * * *